(12) United States Patent
Chen et al.

(10) Patent No.: US 8,299,305 B2
(45) Date of Patent: Oct. 30, 2012

(54) METHOD FOR PREPARING ATOMOXETINE

(75) Inventors: Bo-Fong Chen, Hsinchu (TW);
Yan-Wei Li, Hsinchu (TW); Jinun-Ban Yeh, Hsinchu (TW); Wei-Chyun Wong, Hsinchu (TW)

(73) Assignee: Sci Pharmtech, Inc. (TW)

( * ) Notice: Subject to any disclaimer, the term of this patent is extended or adjusted under 35 U.S.C. 154(b) by 170 days.

(21) Appl. No.: 12/825,582

(22) Filed: Jun. 29, 2010

(65) Prior Publication Data

US 2011/0319664 A1    Dec. 29, 2011

(51) Int. Cl.
*C07C 239/10* (2006.01)
*C07C 239/12* (2006.01)
*C07C 239/20* (2006.01)
*C07C 213/02* (2006.01)
*C07C 213/06* (2006.01)

(52) U.S. Cl. .................. 564/301; 564/347

(58) Field of Classification Search .......... None
See application file for complete search history.

(56) References Cited

U.S. PATENT DOCUMENTS

| 4,868,344 | A | 9/1989 | Brown | |
|---|---|---|---|---|
| 7,294,744 | B2 * | 11/2007 | Baumgarten et al. | 564/358 |
| 7,485,754 | B2 * | 2/2009 | Wang et al. | 564/355 |

FOREIGN PATENT DOCUMENTS

WO    WO 2006/009884    1/2006

* cited by examiner

*Primary Examiner* — Brian J Davis
(74) *Attorney, Agent, or Firm* — Berliner & Associates

(57) ABSTRACT

The present invention provides an efficient method for preparing atomoxetine in high yield. (R)-methylhydroxylaminopropanol compound of formula (II) in the present invention is used as an intermediate without the need for resolution processes.

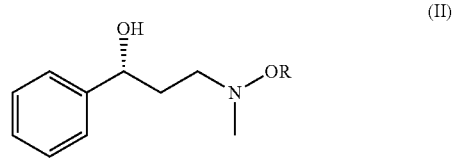

(II)

17 Claims, No Drawings

METHOD FOR PREPARING ATOMOXETINE

BACKGROUND OF THE INVENTION

1. Field of the Invention

The present invention relates to an improved and industrially advantageous method for preparing atomoxetine.

2. Description of Related Art (R)-(−)-N-methyl-3-(2-methylphenoxy)-3-phenylpropylamine (Atomoxetine®) is used for treating attention-deficit hyperactivity disorder (ADHD). It is twice as effective as the racemate and nine times more effective than the (S)-enantiomer.

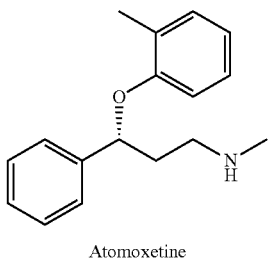

Atomoxetine

There have been several methods reported for preparing (R)-(−)-N-methyl-3-(2-methylphenoxy)-3-phenylpropylamine (Atomoxetine®). For example, U.S. Pat. No. 4,868,344 discloses a process as shown in the following scheme:

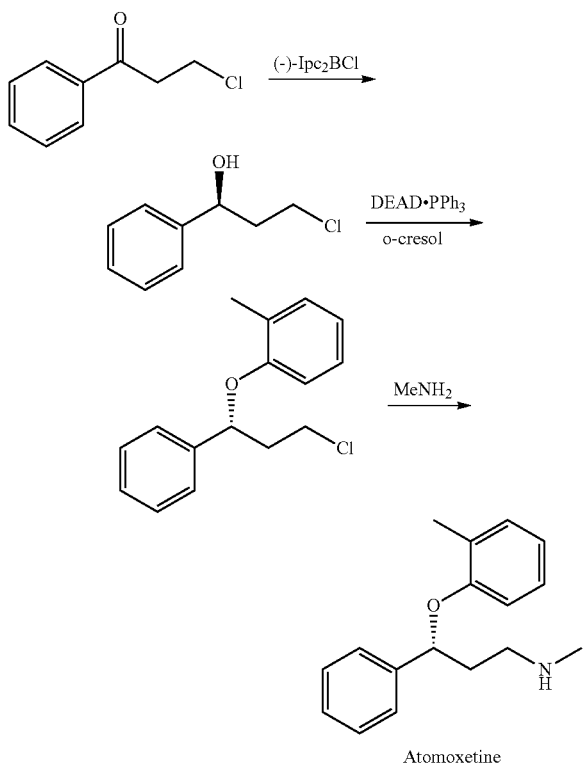

Atomoxetine

In this example, 3-chloropropiophenone is used as the starting material to be asymmetrically reduced with (−)-diisopinocamphenylchloroborane ((−)-IPc$_2$BCl) to give the corresponding chiral alcohol. The resulting chiral alcohol is then reacted with o-cresol via Mitsunobu reaction to form the chiral ether compound. Subsequently, amination of the chiral ether compound with methylamine provided atomoxetine. In this process, the materials such as chiral-borane ((−)-IPc$_2$BCl) and diethyl azodicarboxylate (DEAD) are expensive, and result in high manufacturing cost.

Further, WO 2006/009884 discloses another method for preparing atomoxetine, including the step of reacting N-methyl-3-phenyl-3-hydroxypropylamine with 2-fluorotoluene which is followed by resolution of the resulting product to provide optically pure atomoxetine as shown in the following scheme:

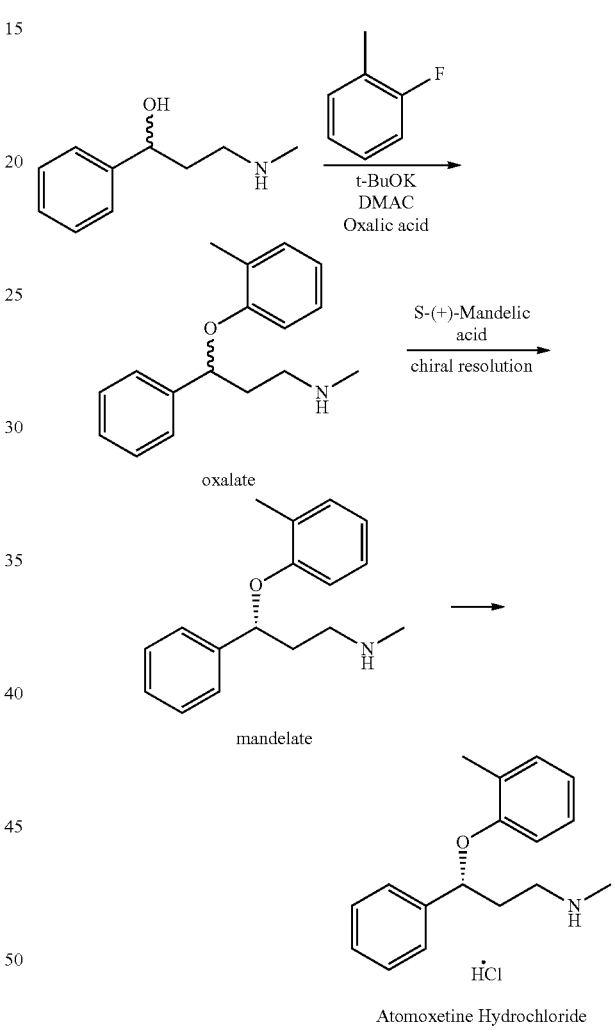

Atomoxetine Hydrochloride

This process involving a chiral resolution step is inefficient due to low product yield, complicated and long time process that renders this process economically less competitive.

Accordingly, the present invention provide a novel method for preparing atomoxetine to overcome the drawbacks of the conventional methods.

SUMMARY OF THE INVENTION

The present invention provides an efficient process for preparing atomoxetine. It is an aspect of the present invention to provide a novel (R)-methylhydroxylaminopropanol compound of formula (II) as the key intermediate

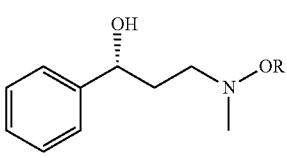

for preparing atomoxetine, wherein R is a hydrogen atom, an alkyl group having 1 to 8 carbon atoms or an aryl group having 6 to 10 carbon atoms. The absolute configuration of the chiral center is R. Furthermore, the present invention provides a ecological and economical method for preparing atomoxetine by using catalytical enantioselective hydrogenation (asymmetric hydrogenation).

To achieve the above-mentioned and other objectives, the method for preparing atomoxetine of the present invention includes steps of: performing a Mannich reaction of acetophenone, formaldehyde and a methylhydroxylamine of formula $HNCH_3(OR)$ to form a substituted amino ketone of formula (I); reducing the substituted amino ketone of formula (I) enatio-selectively to form (R)-methylhydroxylaminopropanol compound of formula (II); performing an N,O-cleavage reaction of the (R)-methylhydroxylaminopropanol compound of formula (II) to form (R)-N-methyl-3-hydroxy-3-phenylpropylamine of formula (III); and performing ether formation of (R)-N-methyl-3-hydroxy-3-phenylpropylamine of formula (III) with 2-fluorotoluene to provide atomoxetine as shown in the following scheme,

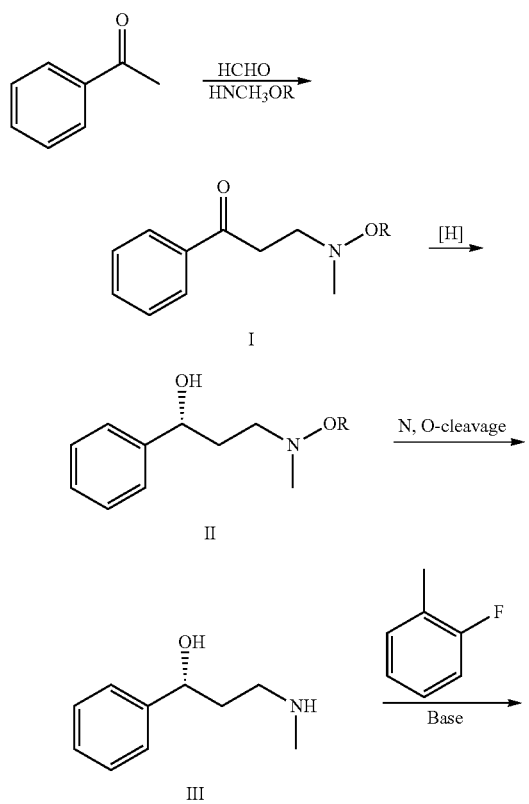

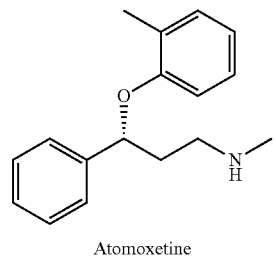

Atomoxetine wherein R is a hydrogen atom, an alkyl group having 1 to 8 carbon atoms or an aryl group having 6 to 10 carbon atoms.

In the following section preferred embodiments are described. However, this is not intended in any way to limit the scope of the present invention.

DETAILED DESCRIPTION OF PREFERRED EMBODIMENTS

The following illustrative embodiments are provided to illustrate the disclosure of the present invention, these advantages and effects can be apparently understood by those in the art after reading the disclosure of this specification. The present invention can also be performed or applied by other different embodiments. The details of the specification may be on the basis of different points and applications, and numerous modifications and variations can be devised without departing from the spirit of the present invention.

The present invention provides a novel (R)-methylhydroxylaminopropanol compound of formula (II) in optical active form:

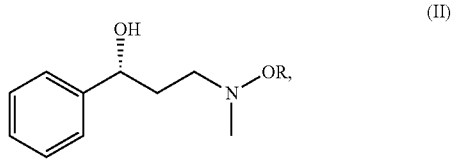

wherein R is a hydrogen atom, an alkyl group having 1 to 8 carbon atoms or an aryl group having 6 to 10 carbon atoms. The absolute configuration of the chiral center is R.

R in the above formula (II) is preferably an alkyl group having 1 to 4 carbon atoms, and is more preferably methyl group.

In addition, the present invention provides the use of (R)-methylhydroxylaminopropanol compound of formula (II) as an intermediate for preparing atomoxetine.

It is known that (R)-N-methyl-3-hydroxy-3-phenylpropylamine formula (III) is an important intermediate for preparing atomoxetine, which is a drug for the treatment of attention-deficit hyperactivity disorder (ADHD). The process for preparing atomoxetine in the present invention is summarized in Scheme 1.

Scheme 1

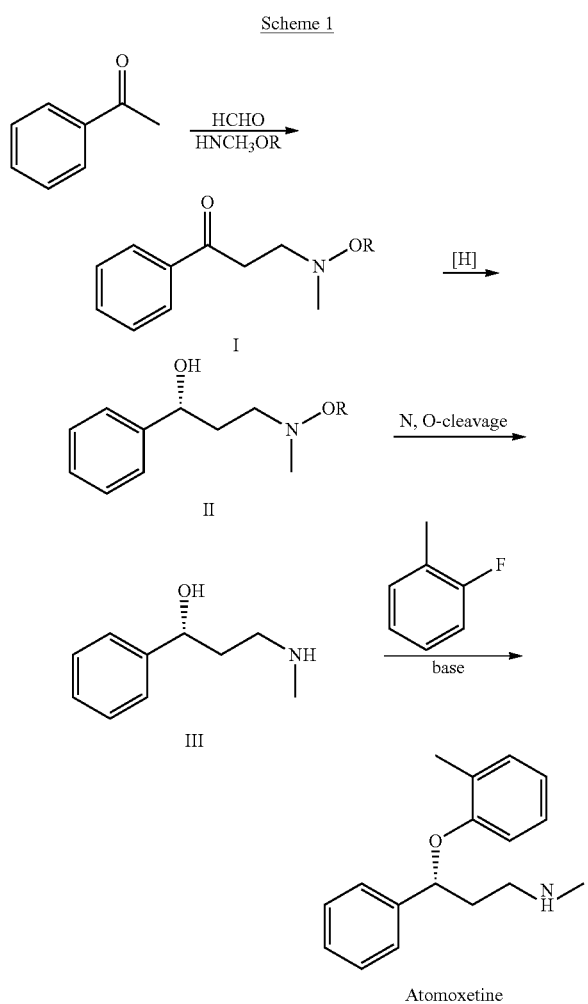

Scheme 1

In Scheme 1, R is a hydrogen atom, an alkyl group having 1 to 8 carbon atoms or an aryl group having 6 to 10 carbon atoms.

In more details, the method of the present invention includes the steps of: (i) performing a Mannich reaction of acetophenone, formaldehyde and a methylhydroxylamine of formula, $HNCH_3(OR)$, to form a substituted amino ketone of formula (I); (ii) reducing the substituted amino ketone of formula (I) enatio selectively to form (R)-methylhydroxylaminopropanol compound of formula (II); (iii) performing an N,O-cleavage reaction of (R)-methylhydroxylaminopropanol compound of formula (II) to form (R)-N-methyl-3-hydroxy-3-phenylpropylamine of formula (III); and (iv) performing ether formation of (R)-N-methyl-3-hydroxy-3-phenylpropylamine compound of formula (III) with 2-fluorotoluene to provide atomoxetine.

The step (i) is carried out at a temperature ranged from 90° C. to 15° C., preferably 80° C. to 40° C., and more preferably 70° C. to 50° C. The substituted amino ketone of formula (I) obtained in the step (i) is either as a free form or as an acid addition salt.

The reduction of the substituted amino ketone of formula (I) in the step (ii) is performed by asymmetric reduction, and the optically active form of the methylhydroxylaminopropanol compound of formula (II) is thus obtained. The optically active form can be obtained via asymmetric hydrogenation using catalyst with chiral ligands or hydride with chiral ligands.

In one preferred embodiment, reduction of the substituted amino ketone of formula (I) in the step (ii) is carried out in a mixture of an alcohol such as methanol and a base such as sodium methoxide, in the presence of chiral catalyst such as $RuCl_2$-((S)-DMSEGPHOS)((S)-DAIPEN). The reaction mixture is hydrogenated at predetermined pressure to yield (R)-methylhydroxylaminopropanol of formula (II) with high ee value.

The N,O-cleavage reaction of the (R)-methylhydroxylaminopropanol compound of formula (II) in the step (iii) is carried out by hydrogenation in the presence of a catalyst such as Raney-nickel, or by chemical reduction methods such as those using $LiAlH_4$ or zinc metal as a reducing agent.

In one preferred embodiment, the (R)-methylhydroxylaminopropanol compound of formula (II) is hydrogenated in methanol in the presence of Raney-nickel at a temperature ranged from 80° C. to 15° C., preferably 70° C. to 40° C., for 9 to 15 hours.

In the step (iv), (R)-N-methyl-3-hydroxy-3-phenylpropylamine formula (III) is reacted with 2-fluorotoluene in the presence of a strong base such as potassium tert-butoxide.

In one preferred embodiment, (R)-N-methyl-3-hydroxy-3-phenylpropylamine formula (III) is reacted with 2-fluorotoluene in a suitable amount of DMSO in the presence of potassium tert-butoxide at a temperature ranged from 20° C. to 110° C., preferably 40° C. to 90° C., for 1 to 24 hours.

Compared with the conventional process, atomoxetine can be obtained optically pure with higher yield and lower cost from the method of the present invention. The following examples are provided merely for illustrative purposes of the present invention and are not to be read as limiting the scope of the present invention, as defined by the appended claims.

EXAMPLES

Example 1

Synthesis of 3-methoxymethylamino-1-phenyl-1-propanone hydrochloride salt

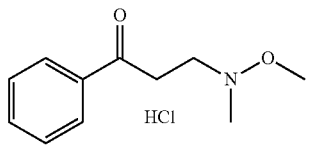

276.0 g of N,O-dimethylhydroxylamine hydrochloride, 101.3 g of paraformaldehyde, 77.4 g of 32% hydrochloride, 374.1 g of 2-acetylthiophene and 800 g of isopropanol were provided into a flask. After being stirred at 70° C. for 13 hours, the reaction mixture was cool down to room temperature. The crystal thus formed was filtered, washed with 700 g of isopropanol and dried under reduced pressure to obtain 569.3 g of 3-methoxymethylamino-1-phenyl-1-propanone hydrochloride salt (87.6%). $^1$H NMR (400 MHz, CDCl$_3$) δ (ppm)= 2.6 (s, 3H), 3.1 (t, J=6.8 Hz 2H), 3.2 (t, J=6.8 Hz 2H), 3.5 (s, 3H), 7.4-7.5 (m, 2H), 7.5 (m, 1H), 8.0 (m, 2H).

Example 2

Synthesis of
(R)-3-methoxymethylamino-1-phenyl-1-propanol

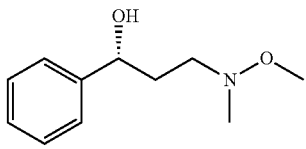

100 mL of degassed methanol solution containing 50 mg of RuCl$_2$-((S)-DMSEGPHOS)((S)-DAIPEN), 47.9 of 3-methoxymethylamino-1-phenyl-1-propanone, and 2.2 g of 30% sodium methoxide methanol solution were provided in a glass autoclave under an argon gas flow. After deaeration and replacement by argon, hydrogen was introduced to a predetermined pressure. The resulting solution was hydrogenated at 20° C. for 12 hours. Upon completion of hydrogenation, the reaction mixture was concentrated to obtain an objective compound as an oily product (47.8 g, 98.8% by HPLC assay, 99% ee). $^1$H NMR (400 MHz, CDCl$_3$) δ (ppm)=1.9 (m, 2H), 2.6 (s, 3H), 2.8 (m, 2H), 3.6 (s, 3H), 4.5 (br, 1H), 4.9 (m, 1H), 7.2-7.4 (m, 5H).

Example 3

Synthesis of
(R)-3-methylamino-1-phenyl-1-propanol

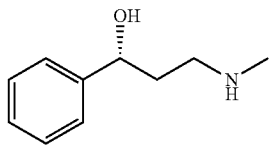

The oily product of (R)-3-methoxymethylamino-1-phenyl-1-propanol obtained in example 2 was dissolved in 100 mL of methanol again with 1.2 g of Raney-nickel in a glass autoclave. The resulting solution was hydrogenated at 50° C. for 12 hours. Upon completion of hydrogenation, the reaction mixture was filtered and the solvent was removed under reduced pressure to obtain an objective compound as an oily compound (39.0 g, 96.5% by HPLC assay, 99% ee). The crude product was further purified by re-crystallization in toluene and heptane with optical purity as high as 100% ee. $^1$H NMR (400 MHz, CDCl$_3$) δ (ppm)=1.7-1.8 (m, 1H), 1.8-1.9 (m, 1H), 2.5 (s, 3H), 2.8-2.9 (m, 2H), 4.9 (dd, J=3, 8.6 Hz, 1H), 7.3-7.4 (m, 5H).

Example 4

(R)-(−)-N-methyl-3-(2-methylphenoxy)-3-phenyl-propylamine (Atomoxetine®)

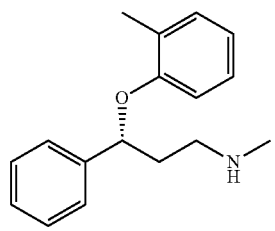

10.0 g of (R)-3-methylamino-1-phenyl-1-propanol, 26.7 g of 2-fulorotoluene and 6.8 g of potassiun tert-butoxide were dissolved in 18.0 g of DMSO, and then heated at 60° C. for 8 hours. After cooling down the reaction, the resulting mixture was extracted with 40.0 g of ethyl acetate and 40.0 g water. The organic layer was extracted with 21.8 g of 10% HCl$_{(aq)}$ to separate atomoxetine from 2-fulorotoluene remained in the reaction. The acidic aqueous layer was basified with 5.5 g of 45% NaOH, then extracted with 40.0 g of ethyl acetate twice. After concentration, crude atomoxetine was obtained as an oily product (14.1 g, 91.0% by HPLC assay, 97% ee).

What is claimed is:

1. An optical active (R)-methylhydroxylaminopropanol compound of formula (II) or its acid addition salts:

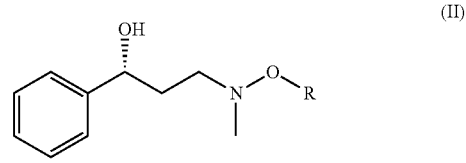

wherein R is a hydrogen atom, an alkyl group having 1 to 8 carbon atoms or an aryl group having 6 to 10 carbon atoms, and an absolute configuration of a chiral center of formula (II) is R.

2. The optical active (R)-methylhydroxylaminopropanol compound of formula (II) according to claim 1, wherein R is an alkyl group having 1 to 4 carbon atoms.

3. The optical active (R)-methylhydroxylaminopropanol compound of formula (II) according to claim 2, wherein R is methyl group.

4. A method for preparing an optical active (R)-methylhydroxylaminopropanol compound of formula (II) or its acid addition salts, comprising the steps of:

performing a Mannich reaction of acetophenone, formaldehyde and a methylhydroxylamine of formula, HNCH$_3$(OR), to form a substituted amino ketone of formula (I)

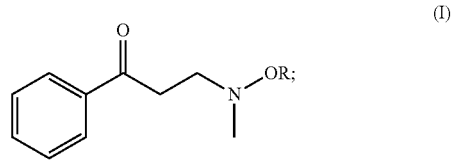

and
reducing the substituted amino ketone of formula (I) enatio selectively to form (R)-methylhydroxylaminopropanol compound of formula (II)

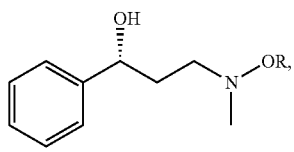

(II)

wherein R is a hydrogen atom, an alkyl group having 1 to 8 carbon atoms or an aryl group having 6 to 10 carbon atoms.

5. The process according to claim 4, wherein the substituted amino ketone of formula (I) is present as a free form or as an acid addition salt.

6. The process according to claim 4, wherein the step of reducing the substituted amino ketone of formula (I) is performed via a hydride reduction with chiral ligands.

7. The process according to claim 4, wherein the step of reducing the substituted amino ketone of formula (I) is performed via asymmetric hydrogenation in the presence of Ru metal with chiral ligands.

8. The process according to claim 4, wherein the step of reducing the substituted amino ketone of formula (I) is performed via asymmetric hydrogenation in the presence of $RuCl_2$-((S)-DMSEGPHOS)((S)-DAIPEN).

9. The process according to claim 8, wherein the step of reducing the substituted amino ketone of formula (I) is performed at a pH value ranged from 6 to 14.

10. The process according to claim 4, wherein the Mannich reaction is performed at a temperature ranged from 90° C. to 15° C.

11. A method for preparing (R)-(−)-N-methyl-3-(2-methylphenoxy)-3-phenylpropylamine, comprising the steps of:
performing a Mannich reaction of acetophenone, formaldehyde and a methylhydroxylamine of formula, $HNCH_3(OR)$, to form a substituted amino ketone of

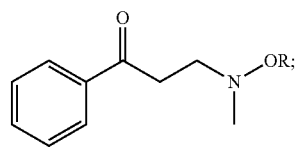

(I)

reducing the substituted amino ketone of formula (I) enatio selectively to form (R)-methylhydroxylaminopropanol compound of formula (II)

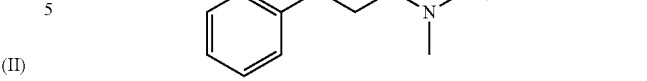

(II)

performing an N,O-cleavage reaction of the (R)-methylhydroxylaminopropanol compound of formula (II) to form (R)-N-methyl-3-hydroxy-3-phenylpropylamine of formula (III)

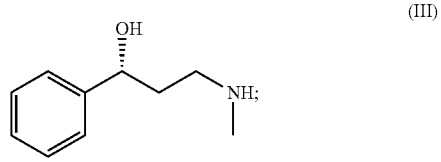

(III)

and
performing ether formation of (R)-N-methyl-3-hydroxy-3-phenylpropylamine of formula (III) with 2-fluorotoluene to provide (R)-(−)-N-methyl-3-(2-methylphenoxy)-3-phenylpropylamine,
wherein R is a hydrogen atom, an alkyl group having 1 to 8 carbon atoms or an aryl group having 6 to 10 carbon atoms.

12. The process according to claim 11, wherein the step of reducing the substituted amino ketone of formula (I) is performed via asymmetric hydrogenation in the presence of Ru metal with chiral ligands.

13. The process according to claim 11, wherein the step of reducing the substituted amino ketone of formula (I) is performed via asymmetric hydrogenation in the presence of $RuCl_2$-((S)-DMSEGPHOS)((S)-DAIPEN).

14. The process according to claim 13, wherein the step of reducing the substituted amino ketone of formula (I) is performed at a pH value ranged from 6 to 14.

15. The process according to claim 11, wherein the N,O-cleavage reaction of the (R)-methylhydroxylaminopropanol compound of formula (II) is carried out by hydrogenation in an alcohol in the presence of Raney-nickel at a temperature ranged from 80° C. to 15° C.

16. The process according to claim 11, wherein the N,O-cleavage reaction of the (R)-methylhydroxylaminopropanol compound of formula (II) is carried out by a chemical reduction using $LiAlH_4$ or zinc metal as a reducing agent.

17. The process according to claim 11, wherein the Mannich reaction is performed at a temperature ranged from 90° C. to 15° C.

\* \* \* \* \*